(12) United States Patent
Deshmukh et al.

(10) Patent No.: US 9,138,137 B2
(45) Date of Patent: *Sep. 22, 2015

(54) INFLATABLE SURGICAL RETRACTOR

(71) Applicant: Dignity Health, Phoenix, AZ (US)

(72) Inventors: Vivek R. Deshmukh, Portland, OR (US); Neil R. Crawford, Tempe, AZ (US)

(73) Assignee: Dignity Health, Phoenix, AZ (US)

( * ) Notice: Subject to any disclaimer, the term of this patent is extended or adjusted under 35 U.S.C. 154(b) by 275 days.

This patent is subject to a terminal disclaimer.

(21) Appl. No.: 13/922,633

(22) Filed: Jun. 20, 2013

(65) Prior Publication Data
US 2013/0317303 A1 Nov. 28, 2013

Related U.S. Application Data

(63) Continuation-in-part of application No. 12/928,615, filed on Dec. 15, 2010, now Pat. No. 8,491,471, which is a continuation-in-part of application No. 12/393,568, filed on Feb. 26, 2009, now abandoned, which is a continuation of application No. PCT/US2007/019198, filed on Aug. 31, 2007.

(60) Provisional application No. 61/721,561, filed on Nov. 2, 2012, provisional application No. 60/824,234, filed on Aug. 31, 2006.

(51) Int. Cl.
*A61B 1/32* (2006.01)
*A61B 17/02* (2006.01)
*A61B 17/00* (2006.01)
*A61B 1/313* (2006.01)

(52) U.S. Cl.
CPC ............... *A61B 1/32* (2013.01); *A61B 17/0218* (2013.01); *A61B 1/3132* (2013.01); *A61B 17/02* (2013.01); *A61B 17/0293* (2013.01); *A61B 2017/00557* (2013.01); *A61B 2017/00871* (2013.01); *A61B 2017/00955* (2013.01); *A61B 2017/0225* (2013.01)

(58) Field of Classification Search
CPC ............... A61B 17/02; A61B 17/0218; A61B 2017/00557; A61B 2017/0225; A61B 2017/00955; A61B 1/32
See application file for complete search history.

(56) References Cited

U.S. PATENT DOCUMENTS

| | | |
|---|---|---|
| 3,618,614 A | 11/1971 | Flynn |
| 4,098,159 A | 7/1978 | Rothfuss |
| 4,149,852 A | 4/1979 | Tiru et al. |
| 4,584,326 A | 4/1986 | Flynn |
| 4,669,105 A | 5/1987 | Fenster et al. |
| 4,984,564 A | 1/1991 | Yuen |
| 5,078,134 A | 1/1992 | Heilman et al. |

(Continued)

OTHER PUBLICATIONS

Feb. 29, 2008 International Search Report for PCT/US07/019198.
(Continued)

*Primary Examiner* — Ellen C Hammond
(74) *Attorney, Agent, or Firm* — Hahn Loeser & Parks LLP

(57) ABSTRACT

For minimally invasive surgical applications, an expandable surgical retractor is inserted in a surgical corridor and expanded to a desired size and shape. Cooling allows the retractor to maintain the expanded characteristic. Following surgery, the retractor can be removed in a manner that minimizes bleeding and tissue damage.

25 Claims, 20 Drawing Sheets

(56) References Cited

U.S. PATENT DOCUMENTS

| | | |
|---|---|---|
| 5,460,170 A | 10/1995 | Hammerslag |
| 5,496,345 A | 3/1996 | Kieturakis et al. |
| 5,868,775 A | 2/1999 | Bircoll |
| 5,976,078 A | 11/1999 | Bridges |
| 6,162,172 A | 12/2000 | Cosgrove et al. |
| 6,187,000 B1 | 2/2001 | Davison et al. |
| 8,052,599 B2 | 11/2011 | Cohen |
| 8,282,548 B2 | 10/2012 | Kelner |
| 2004/0097792 A1 | 5/2004 | Moll et al. |
| 2004/0260328 A1 | 12/2004 | Zvuloni et al. |
| 2005/0216002 A1 | 9/2005 | Simonson |
| 2005/0277946 A1 | 12/2005 | Greenhalgh |
| 2007/0032703 A1 | 2/2007 | Sankaran et al. |

OTHER PUBLICATIONS

Feb. 29, 2008 Written Opinion of the International Searching Authority for PCT/US07/019198.

Jun. 10, 2011 Office Action in connection with prosecution of U.S. Appl. No. 12/393,568.

Sep. 13, 2012 Office Action in connection with prosecution of U.S. Appl. No. 12/393,568.

Jan. 7, 2013 Office Action in connection with prosecution of U.S. Appl. No. 12/393,568.

Jan. 14, 2013 Office Action in connection with prosecution of U.S. Appl. No. 12/928,615.

"Medtronic METRx™ MicroDiscectomy System" (Medtronic, Inc. 2011) (13 pgs. available at http://wwwp.medtronic.com/Newsroom/ImageLibraryDetails.do?itemID= --- .)

"Thermal Analysis of Polyvinyl Chloride" (Application Brief TA No. 65, pp. 1-2) (SII Nano Technology Inc., Feb. 1995).

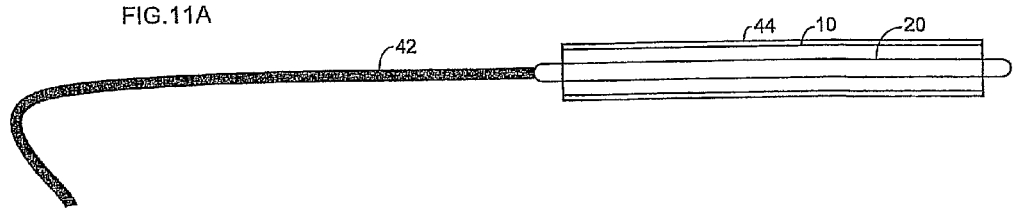
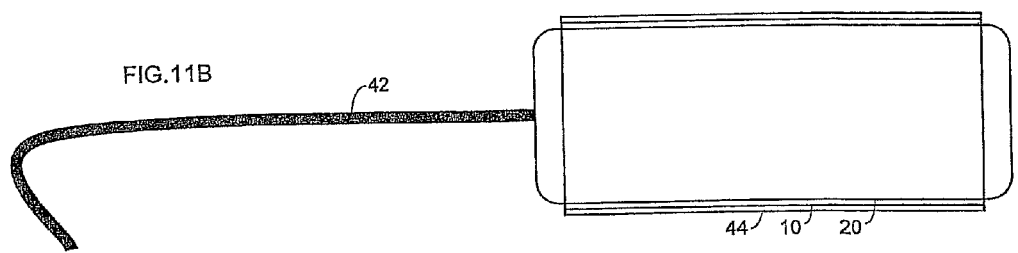
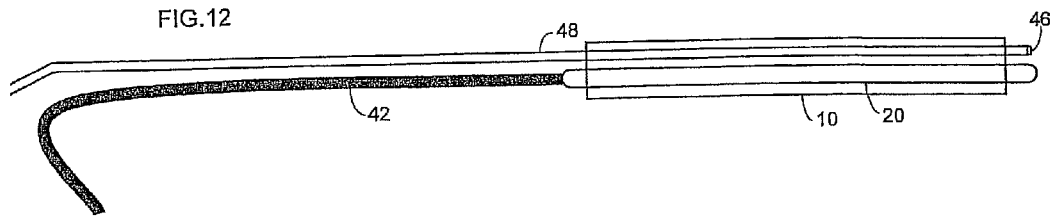

INFLATABLE SURGICAL RETRACTOR

CROSS-REFERENCE TO RELATED APPLICATIONS

This application claims the benefit of the filing date of U.S. provisional application Ser. No. 61/721,561, filed 2 Nov. 2012, and also is a continuation-in-part of co-pending application Ser. No. 12/928,615, filed 15 Dec. 2010, which is a continuation-in-part of application Ser. No. 12/393,568, filed 26 Feb. 2009, which is a continuation of international application no. PCT/US2007/019198, filed 31 Aug. 2007, which claims the benefit of the filing date of U.S. provisional application Ser. No. 60/824,234, filed 31 Aug. 2006. The contents of the above-mentioned prior applications are incorporated by reference into this application.

FIELD OF THE INVENTION

The present invention concerns surgical devices used to maintain a surgical corridor. More particularly the present invention concerns a retractor comprising a thermally responsive material that permits the creation of a stable opening through which surgery can be performed.

BACKGROUND

It is desirable when surgery is required, or in any medical procedures, to be as minimally invasive as possible. The well being of the patient and speed of recovery are often dependent on the degree to which a procedure is quickly and accurately accomplished, with as little damage to the body and with as little blood loss as possible. For this reason laparoscopic and other minimally invasive surgical procedures have gained considerable favor among health care professionals.

Providing surgical procedures with minimally invasive openings from the skin, or other surface, to the point of surgical interest will tend to aid in the rapid recovery of the patient. The use of modern surgical techniques, including laparoscopy, fluoroscopy, MRI, CT and other methods of viewing and working within the operating theater, have made a significant difference in the quality and speed of patient recovery.

However, techniques for accomplishing such surgery have often been hampered by the need to provide a stable opening from an outer surface, such as the skin or the muscle through to the area of surgical interest, without causing damage to tissue there between. Presently it is necessary to form an incision and then, by using mechanical retractors, pull back and hold an opening open throughout the surgical procedure. Such use of mechanical retractors tends to cause damage to skin surfaces and increases the time of recovery and the pain that the patient feels. Further, the size of the incision needed to create the appropriately sized opening through which surgery will proceed can increase the amount of bleeding and oozing in the wound, cause tears in skin and muscle and provide a site for post-operative infections.

One method for creating a smaller surgical corridor without using claw-like mechanical retractors is through the use of sequential dilator tubes. In this method, a small incision is made and a small post is first inserted to the necessary depth, after which a series of larger and larger tubes is forced into place over the initial guide post. Finally, the central tubes and post are removed, leaving only the outer tube as a corridor through which to perform minimally invasive surgery. This method, embodied by the Metr'x system (Medtronic), has the problem that each additional tube can potentially damage the surrounding musculature, connective tissue, and nerves through a shearing action as it is slid into place, especially as the tension on the retracted tissues becomes greater and greater with each dilation.

It is desirable to conduct a surgical procedure using modern minimally invasive methods while providing a stable opening that can be made with minimal damage to the surrounding tissue.

BRIEF DESCRIPTION OF THE DRAWINGS

The drawings are for illustrative purposes, and are not necessarily drawn to scale.

FIG. 11A is a schematic representation of a balloon retractor device with the tube surrounded by a thermal barrier.

FIG. 11B is a schematic representation of the balloon retractor device of FIG. 11A with the balloon inflated.

FIG. 12 is a schematic representation of a balloon retractor device with a sensor at the distal end of the tube.

DETAILED DESCRIPTION OF SOME EMBODIMENTS

Figure 1:
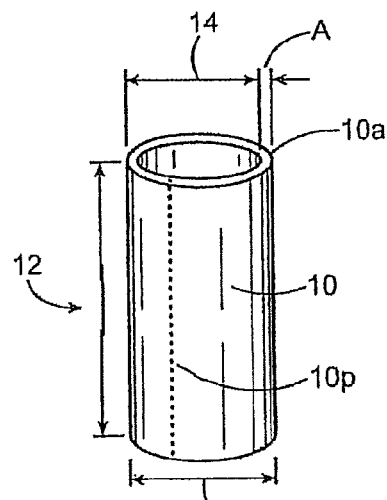
FIG. 1 is perspective view of an example of a retractor made in accordance with the teachings of the present invention.

A minimally invasive surgical retractor is provided for creating and maintaining an enlarged surgical corridor. The retractor is expandable, preferably in form of an inflatable balloon retractor that can be inserted in a surgical corridor and expanded to a desired size and shape. For example, the retractor comprises a tube of thermally responsive material having a length sufficient to span from a skin surface through to a point of surgical interest. For example, it is amenable to many shapes, including cylindrical, conical with the base at the depth of the corridor, hourglass, crescent, etc., as dictated by the surgeon's needs. The thermally responsive material is pliable and expansive when heated above body temperature and becomes rigid when cooled to body temperature, such that the tube can be heated to pliability and inserted into a narrow opening in the skin and through to the point of surgical interest. The tube can be expanded by expanding means while pliable and in situ and then cooled or allowed to cool so as to maintain the enlarged opening, thereby forming a surgical corridor.

In some embodiments, the thermally responsive material becomes pliable at between about 5° F. and about 60° F. above body temperature and in some embodiments the thermally responsive material is a thermoplastic material. As another example, the thermally responsive material also can be a shape memory alloy (SMA). Such a material has similar properties as a thermoplastic material, in that the SMA becomes pliable when melted and can be stretched. It holds its shape when cooled and, in the absence of external forces, returns to the original shape when heated. As compared to a thermoplastic retractor, an SMA retractor would have greater strength per unit volume. This material property permits thinner walls and better thermal conductivity, enabling faster setting/softening. An SMA retractor also could be formed either as a smooth tube, or as a meshed tube (similar to a Chinese finger toy) which would be useful for keeping the device positioned in the tissues where desired without slipping.

To aid in viewing the device in situ the thermally responsive material can be made, coated, or embedded with a radio-opaque material such that it is viewable in fluoroscopy. Alternatively, it could have radio-opaque gradation lines, separated by a known distance, enabling the surgeon to visualize the current depth of insertion and necessary further depth of insertion relative to tissues visualized on the image. In such embodiments, the thermally responsive material can be of a type that is radio-opaque in both pliable and rigid states, or radio-opaque in its pliable shape to facilitate insertion, and radiolucent in its rigid state so as not to obstruct visualization of tissues, tools, and implants during surgery. In some embodiments, the distal tip can be made radio-opaque to allow fluoroscopic verification of its placement in situ.

A method of expanding and fixing the circumference of a surgical corridor can comprise the step of providing one or more tubes of thermally responsive material, as described above, having either solely or in unison a length sufficient to span from an entry point of a patient to a point of surgical interest. For example, a second retractor can be placed at a greater depth through the first retractor, using a "telescoping" effect. The method can further comprise heating the one or more tubes so as to make them pliable and expandable and inserting the heated, one or more tubes between the entry point, such as at a skin surface, and the point of surgical interest. The method can further comprise expanding the one or more tubes to form, solely or in unison, a surgical corridor between the entry point and point of surgical interest through which surgery may proceed.

Following surgery, such retractor(s) can be quickly and easily removed in a manner that minimizes bleeding and tissue damage. One such method comprises reheating to soften and restore the retractor to its unexpanded size, taking advantage of the material property of both thermoplastics and SMAs whereby they return to their original size when reheated. Furthermore, retractor surfaces can be treated, prior to insertion, to help stave infection and provide a quicker recovery with faster healing. In one method, laterally placed perforations allow for fracturing of the retractor by Bovie® cautery, facilitating removal by "unzipping" the retractor.

A device can be used to help perform all of the heating, expansion and cooling functions to the retractor. It can be an expansion device that includes means to provide a heated solution, expansion capabilities, and a cooling solution sequentially to create the necessary pliability, to enlarge the retractor and then to cool the retractor to fix it into position during the surgical procedure.

A more detailed explanation follows with reference to the accompanying drawings.

While the present invention is susceptible of embodiment in various forms, there is shown in the drawings a number of embodiments that are discussed in greater detail hereafter. It should be understood that the present disclosure is to be considered as an exemplification of the present invention, and is not intended to limit the invention to the specific embodiments illustrated. It should be further understood that the title of this section of this application ("Detailed Description of Some Embodiments") is not intended to limit the subject matter disclosed herein.

Figure 1A:
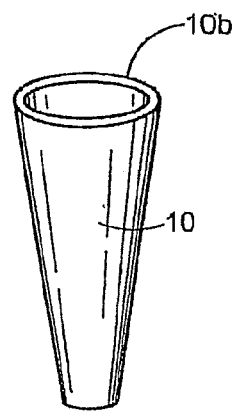
FIGS. 1A-1C are perspective views of other examples of retractors made in accordance with the teachings of the present invention.
Figure 1B:
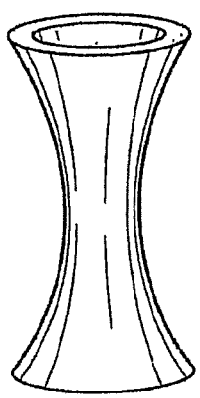
Figure 1C:
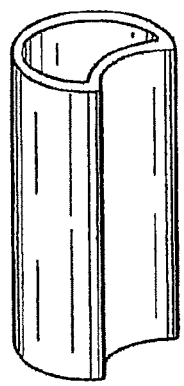

Referring to the drawings, specifically FIG. 1, a tube 10 of thermally responsive material, such as a thermoplastic or an SMA, is provided, having a length 12, an initial internal diameter 14 and an initial external diameter 16. The initial inner and outer diameters, 14, 16, of tube 10 define a tube thickness "A". Tube 10, while shown as generally cylindrical, in FIG. 1, can be made such that it is generally conical, as shown in FIG. 1A, or in many other shapes, including for example the shapes shown in FIGS. 1B and 1C as will be understood by persons having ordinary skill in the art. Although it should be understood that the final shape of the expanded tube 10 is affected by the expansion mechanism by which the tube is expanded—such as by the shape of a balloon 20, some consideration must be made with regard to wall thickness in various regions of the tube 10 so that the desired shapes can be achieved.

Figure 6:
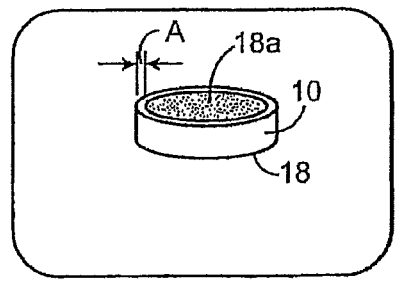
FIG. 6 is a schematic representation of an expanded retractor within the surgical corridor.

In one embodiment of the present invention, tube 10 is comprised of a rigid material that becomes pliable upon heating. Tube 10 can be heated, as will be discussed in greater detail below, until it reaches a desired state of pliability, such that the inner diameter 14 can be expanded to create an enlarged surgical corridor 18a as shown in FIG. 6. A pliable tube 10 may be introduced into a surgical corridor 18 with a low compliance balloon 20 (of a balloon catheter 20a) of the type used in other surgical procedures such as balloon angioplasty, fitted within the tube 10. It will be understood by persons having ordinary skill in the art that a combined tube 10 and balloon catheter 20a, or balloon retractor device 25, can also be prepared together as a single surgical device.

Figure 2:
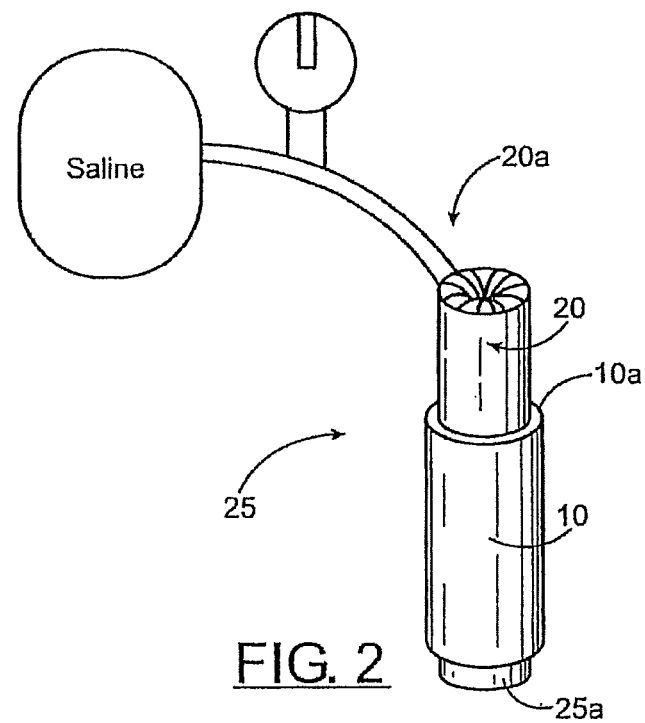
FIG. 2 is schematic view of a retractor of FIG. 1 associated with an expansion device to make a balloon retractor device.
Figure 3:
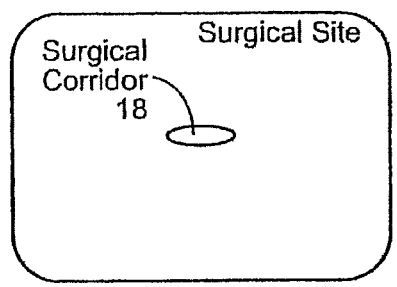
FIG. 3 is a schematic representation of a surgical site, with a surgical corridor formed therein.
Figure 4:
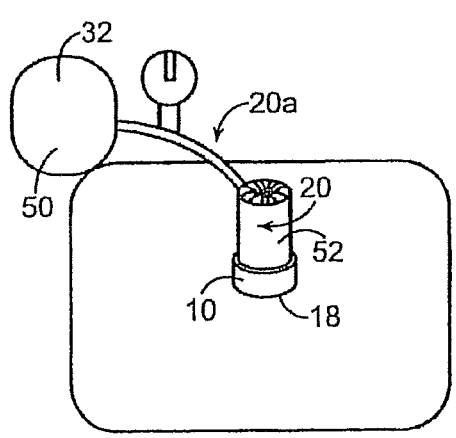
FIG. 4 is a schematic representation of a retractor and expansion device inserted together within the surgical corridor in an unexpanded state.
Figure 5:
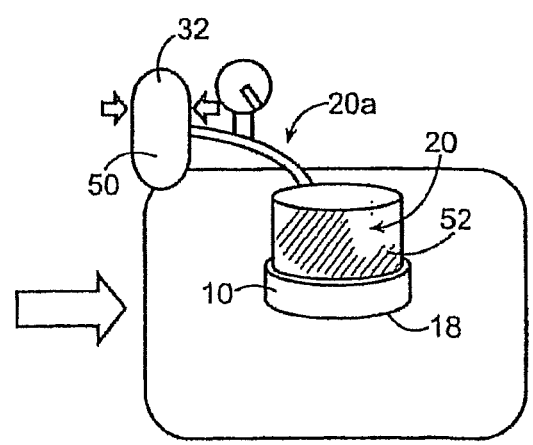
FIG. 5 is a schematic representation of a balloon retractor device inserted within the surgical corridor in an expanded state.

FIG. 2 is schematic view of a retractor of FIG. 1, associated with an expansion device to make a balloon retractor device. FIG. 3 is a schematic representation of a surgical site, with a surgical corridor formed therein. FIG. 4 is a schematic representation of a retractor and expansion device inserted together within the surgical corridor in an unexpanded state. FIG. 5 is a schematic representation of a balloon retractor device inserted within the surgical corridor in an expanded state.

Once tube 10 has been introduced into the surgical corridor 18 the balloon 20 can be filled with liquid or gas, through a syringe or other pressure forming means, causing expansion of the pliable tube 10. A gas may be advantageous in the event that the balloon ruptures, but it is easier to control the temperature and pressure of a liquid. The walls 10a can be expanded to a desired size before allowing tube 10 to cool. Once cooled, tube 10 will be relatively rigid and the desired size will be maintained. For example, an initial outer diameter 16 of about 12 mm can be expanded to about 25 mm. The balloon 20 can then be deflated and removed thereby creating a surgical corridor 18a, FIG. 6, of a size and shape appropriate for the particular application. A blunt distal tip 25a may facilitate insertion of the balloon retractor device 25 into the surgical incision. Lubricating the balloon 20 with a biocompatible material before inflating it will make it easier to extract the balloon 20. It will be understood by persons having skill in the art that the size of the surgical corridor 18a will be determined by the judgment of the surgeon and that a larger or smaller corridor can be made as needed without departing from the novel scope of the present invention.

It will be understood, by persons having ordinary skill in the art, that preferred material for tube 10 will be relatively pliable at a determined temperature range and relatively rigid at a lower temperature. In one embodiment, tube 10 can be comprised of thermoplastic material. Thermoplastics that become pliable around 5° F. to 60° F. higher than body temperature (about 98° F. or 37° C.) and rigid upon cooling are preferred. Protoplast™, a polycaprolactone (PCL) product of ProtoPlast, Inc. of Ontario Canada, is an exemplary commercially available thermoplastic with a transition temperature of about 140° F. Ecorene™, a polylactic acid (PLA) product of ICO Polymers, is another commercially available thermoplastic with transition temperature of about 50° C. Aquaplast™ is a thermoplastic product of WFR-Aquaplast that is commercially available with a transition temperature of about 50° C. and with a shape memory that causes the product to return to its original size after reheating.

Figure 17:
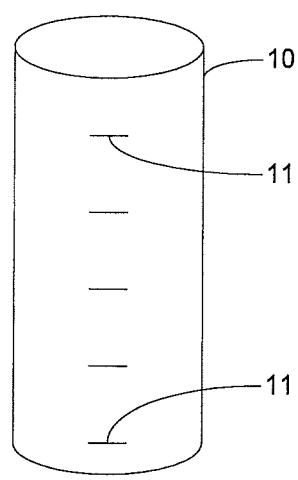
FIG. 17 is a perspective view of a retractor tube with a representation of radio-opaque gradation lines.

In another embodiment, tube 10 can be comprised of, embedded with, or coated with a radio-opaque material, thereby allowing a surgeon to easily see, on fluoroscopy, whether tube 10 has been installed appropriately before and/ or after inflation. Alternatively, it could have radio-opaque gradation lines 11, separated by a known distance, as represented in FIG. 17. This would enable the surgeon to visualize the current depth of insertion and necessary further depth of insertion relative to tissues visualized on the fluoroscopic image. In another embodiment, the distal tip 25a of the balloon retractor device 25 may be comprised of a radio-opaque material or have a radio-opaque material such as a small metallic ball embedded, allowing fluoroscopic verification of the appropriate surgical site level.

Figure 2A:
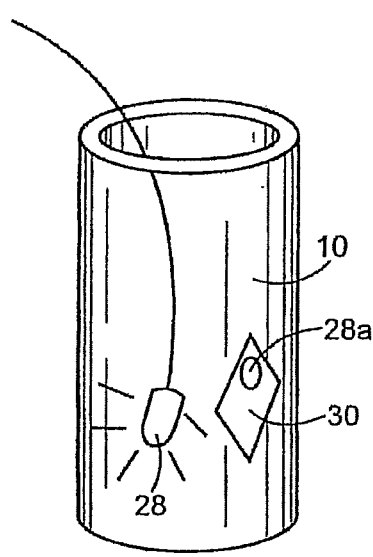
FIG. 2A is a schematic view of a retractor of FIG. 1 associated with a light source and a light sensor.

The translucence of tube 10 can also assist the surgeons and attendants with an automation of the device. In another embodiment, shown in FIG. 2A, a small light 28, such as an LED, fiber optic cable or laser, and an accompanying optical sensor 30, fitted in tube 10, can be used to sense the wavelength of light reflected from tube 10. The light sensor 30 can indicate, for example by an indicator light 28a, when the walls 10a are opaque or translucent.

The presence of blood and other obstructions may impair the ability to detect changes between transparency, translucence and opaqueness. In another embodiment, a thermochromic coating on tube 10 or a thermochromic component in the material comprising tube 10 can be used. Such thermochromic substances change color according to temperature and will enhance the ability detect when temperature thresholds are crossed. Such thermochromic substances are available, for example, from Kelly Chemical Corporation (www.kellychemical.com). It identifies various thermochromic pigments (at www.kellychemical.com/english/page/products/pigments/thermochromic.htm, for example), and appropriate substances can be selected to achieve a suitable color change at a desired temperature range. During the deployment phase, such a visual cue makes it easier for the surgeon to know when the tube 10 is rigid and it is acceptable to deflate and remove the balloon 20. During the removal phase, such a visual cue makes it easier for the surgeon to know when the tube 10 has changed back to a pliable state and it is safe to extract the device.

The shape of tube 10 can vary depending on the application and includes cylindrical, conical, as shown in FIGS. 1 and 1A, respectively, with the base 10b of the cone placed so that it is at the depth of the surgical corridor that is the site of surgical interest. Other shapes, including hourglass or bowtie (FIG. 1B) and crescentic (FIG. 1C), are possible as well. The shape of tube 10 may be dictated by the shape of the balloon 20 in an expanded state or the differential composition of tube 10 which allows for preferential expansion in a particular location or direction. In one embodiment, tube 10 is cylindrical in shape. In some applications, however, it may be desirable to utilize a retractor with, for example, an hourglass or bowtie shape instead of a cylinder. An hourglass shape would be less vulnerable to displacement during surgery. A conical shape with the base at the depth of the field allows the surgeon to improve surgical exposure at the point of pathology while maintaining a small skin incision. The area and angles of exposure are greatly increased without enlargement of the skin incision. Simply manipulating the operating table or the surgical microscope facilitates the operative exposure. A crescent shape allows the surgeon to specifically enlarge the area of exposure in a given direction and minimizes unnecessary exposure. In some cases, a non-cylindrical retractor can be used to improve the strength of tube 10 in the hardened state. The composition of tube 10 can be selected to influence the final shape and strength of the expanded retractor. In one embodiment, the thickness of tube 10 is non-uniform such that an applied force at the interior of tube 10 will result in differential expansion of the walls to achieve a desired final shape.

In another embodiment, tubes 10 are comprised of a mixture of materials with different elasticity properties. The material mixture may be uniform or vary along a linear axis. In one embodiment of the invention, a ring of material with relatively low elasticity can be placed at the midpoint of a cylindrical, unexpanded retractor. A cylindrical balloon 20 used to expand tube 10 will achieve greater expansion of the walls where the resistance to the applied force is less. In an expanded condition, the center portion of tube 10 will have a smaller diameter than the proximal and distal portions. Consistent with the scope of the invention, the shape of tube 10 in an unexpanded and in an expanded state can vary to accommodate any application and is not limited by specific embodiments described. Furthermore, it will be apparent to one skilled in the art that the composition and physical characteristics of tube 10 may be varied in any way to achieve a desired shape.

As described, heating of tube 10 enhances pliability. In one embodiment, tube 10 is heated to increase pliability prior to insertion in the surgical corridor. Tube 10 can be heated in a sterile hot water bath prior to insertion. Alternatively, tube 10 can be heated by introducing a liquid of an appropriate temperature into a balloon fitted within tube 10. It will be readily apparent to one skilled in the art that in appropriate circumstances tube 10 can be inserted into the surgical corridor in a relatively rigid state and pliability obtained by infusing liquid in the balloon 20 after insertion. Heating of tube 10 can be accomplished in any manner consistent with sterile surgical practices and is not limited to the provided descriptions.

Figure 1D:
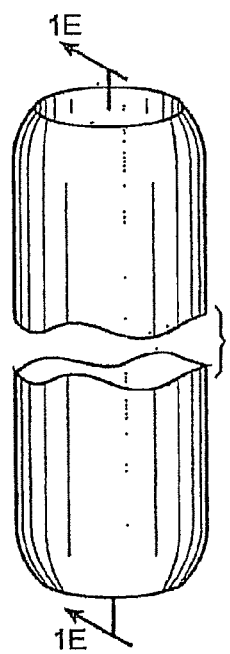
FIG. 1D is a perspective view, partially broken away to show length, of another example of a retractor made in accordance with the teachings of the present invention.
Figure 1E:
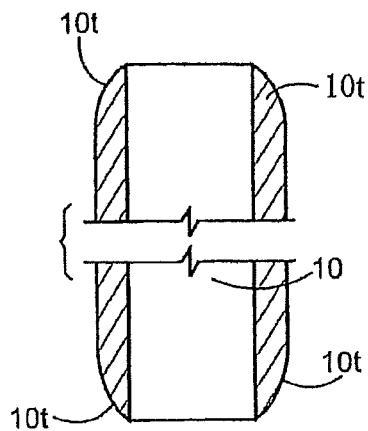
FIG. 1E is a cross-sectional view of a portion of the retractor of FIG. 1D, taken along the line 1E-1E thereof.
Figure 1F:
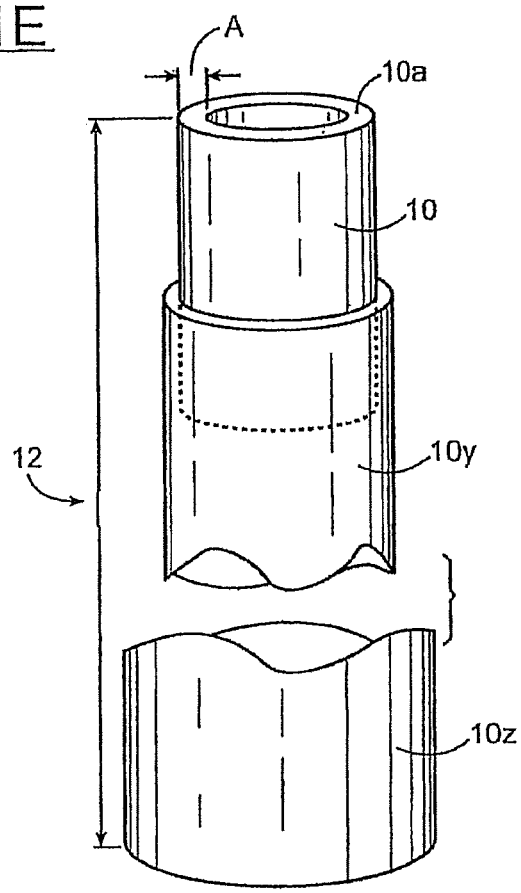
FIG. 1F is a perspective view, partially broken away to show length, of an example of a number of retractors made in accordance with the teachings of the present invention shown fitted together to show a method of increasing the length of a surgical corridor.

The length 12 of tube 10 can also be varied depending on the application (see FIG. 1F). Because deformation of tube 10 will tend to occur radially, the overall length of tube 10 can be made relatively constant compared with the radial deformation. The length of the cylinder can, therefore, be selected by the surgeon to best suit the depth of retraction needed. Tube 10 length may be determined by the surgeon with the use of a depth gauge placed during the initial dissection. This depth gauge may also serve the dual purpose of allowing for fluoroscopic localization. In one embodiment, the surgeon can "telescope" retractor devices one partially within another. In one application, a first superficial corridor can be made and a retractor placed to the bottom of the initial dissection and expanded. Then, working within the proximal corridor, a more distal corridor is prepared that is continuous with the proximal corridor.

A second retractor 10y can then be placed deeper than the full extent of the first retractor and expanded such that the proximal few millimeters of the new retractor is in contact with the distal few millimeters of the first retractor. This sequence may continue to whatever final depth is needed. Telescoping allows the surgeon to carry out the procedure in steps conforming to the existing anatomic planes. For example, the first retractor 10 can be placed to the level of the fascia, retracting skin and subcutaneous fat. A fascial incision is then made, and a second and/or third retractor 10y-10z is telescoped to retract the fascia, muscle, and deep tissues. This sequence leads to exposure of the pathology of interest. Telescoping is particularly useful for the obese patient where a single size does not provide adequate depth of exposure. In one application, the interface between consecutive retractors can be made smooth by allowing an inflatable balloon to expand and deform the malleable retractor walls at the junctions to create smooth joints between telescoping retractors.

Other characteristics of tube 10 may be modified for specific applications. For example, in one embodiment shown in FIGS. 1D and 1E, the walls of tube 10 may be beveled 10t at the leading and trailing edges. A beveled leading edge may be desirable in some applications where the unexpanded device must be forced through a narrow initial corridor and a blunt leading edge would make this initial insertion difficult. A beveled trailing edge of tube 10 may also be desirable in some applications to prevent formation of a blunt trailing edge after expansion that may interfere with introduction of surgical instruments or additional retractors.

Tube 10 can also be fitted with a balloon 20. In one embodiment, a balloon 20 can be used to expand the pliable retractor walls 10a after insertion in the surgical corridor 18. In some applications, bulging of the balloon at the proximal and distal ends of tube 10 may reduce the efficiency of the balloon in producing the desired radial or outward expansion of the walls. The elasticity of the balloon can be chosen to reduce or prevent undesirable bulging. For example, the balloon can be comprised of cloth, such as is used for blood pressure cuffs, or an inelastic plastic film commonly used in some catheter applications. When choosing balloon material, the thermal gradient across the balloon also can be considered. For example, if the transition temperature of tube 10 is 140° F. but the thermal gradient across the balloon membrane is 20° F., then the liquid within the balloon needs to be at 160° F. if the balloon is being used to cause transitioning for expansion or removal of tube 10 (as described below).

The shape of the balloon will influence the final shape of tube 10. One skilled in the art will see that a variety of balloon shapes may be used depending on the circumstances and applications. In one embodiment, a cylindrical balloon 20 is used to create cylindrical retractor walls and a corresponding cylindrical surgical corridor 18. In other applications, conical or crescent shaped balloons may be used, depending on the application. In still other embodiments, the balloon may be shaped to allow for tapering at the proximal and/or distal ends of tube 10. An outward tapered end, or more of an hourglass/bowtie shape instead of a cylinder, may be a desirable retraction shape that can have a beneficial role in maintaining a stable retractor position superior to a straight cylinder. One skilled in the art will see that the applications and balloon shapes are not limited by the disclosures.

Figure 8:
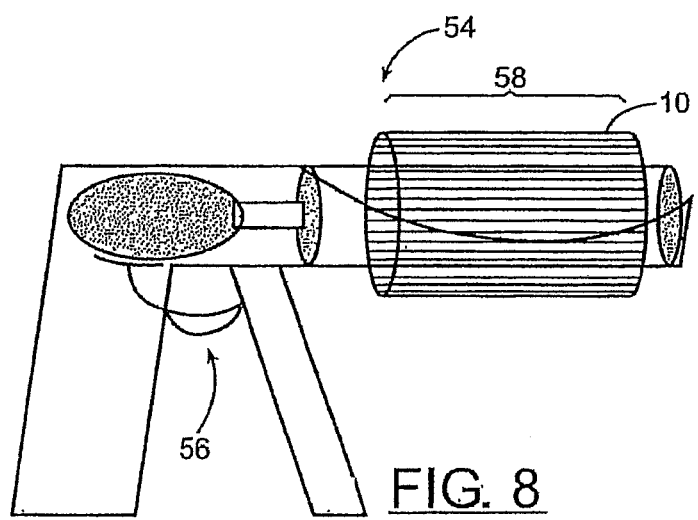
FIG. 8 is a schematic view of another device for expanding a retractor of the present invention.
Figure 9:
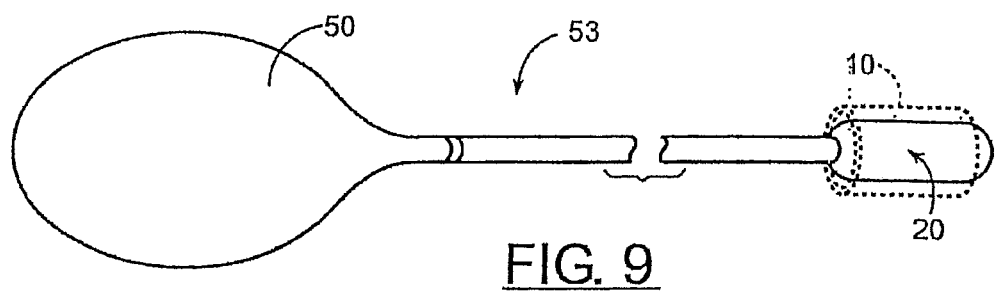
FIG. 9 is a perspective view of another device for expanding a retractor of the present invention.

As previously described, a fluid 32 can be used to fill and expand the balloon. In some embodiments, a saline solution is used to protect the patient in the case of accidental rupture of the balloon material. The saline solution in some embodiments is introduced using technology similar to that currently used for inflating low compliance balloon catheters with pressurized saline. Alternatively, saline solution may be delivered via an infusion pump syringe controlled with on/off forward/reverse switches (not shown). In yet another embodiment of the invention, shown in FIG. 9, a simple squeeze bag 50 that the operator manually compresses may be used to eject saline solution or some other fluid from a bag and into the insufflator 53. In another embodiment, shown in FIG. 8, tube 10—balloon construct can be loaded onto the shaft of a hand-held device 54 shaped like a "gun." The trigger 56 is coupled with balloon inflation. The surgeon places the construct 58 within the wound and deploys tube 10 by pulling the "trigger." A new retractor 10 can be loaded for a second deployment.

Figure 18A:
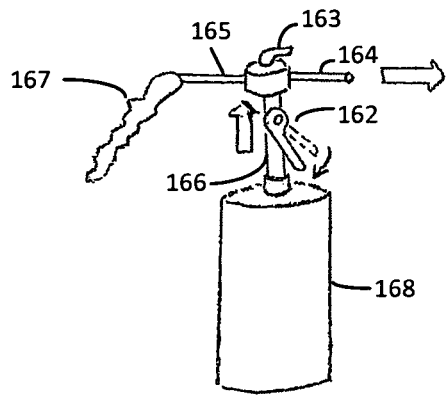
FIG. 18A is a schematic representation of a balloon inflation/deflation mechanism operating to inflate a balloon.
Figure 18B:
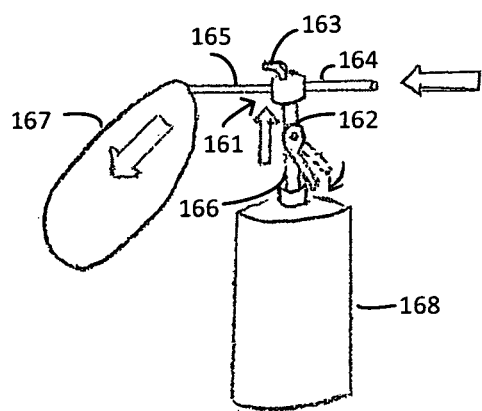
FIG. 18B is a schematic representation of the mechanism of FIG. 18A operating to deflate a balloon.

In an embodiment shown in FIGS. 18A and 18B, a balloon inflation/deflation mechanism 161 includes trigger 162, valve 163, and three connecting channels 164, 165 and 166. Channel 164 connects to a proximal end of a balloon. Channel 165 connects to a waste depository 167. Channel 166 connects to an aerosol source 168, such as a can of pressurized biocompatible refrigerant in a liquid state. When released through valve 163, the refrigerant vaporizes and cold gas is expelled. Trigger 162 is not necessarily a mere on/off switch, but can be used to release a measured quantity of gas to inflate or deflate the balloon. When valve 163 is positioned for balloon inflation, cold gas enters the balloon as illustrated in FIG. 18A. When valve 163 is positioned for deflation, cold gas is expelled to waste depository 167, pulling a vacuum on the balloon as illustrated in FIG. 18B. A common method for creating this vacuum is to divert gas flow through a Venturi tube, which takes advantage of the Venturi effect.

As discussed above and as will be readily seen by one skilled in the art, introduction of a fluid into the balloon can be accomplished in a variety of ways.

Figure 7:
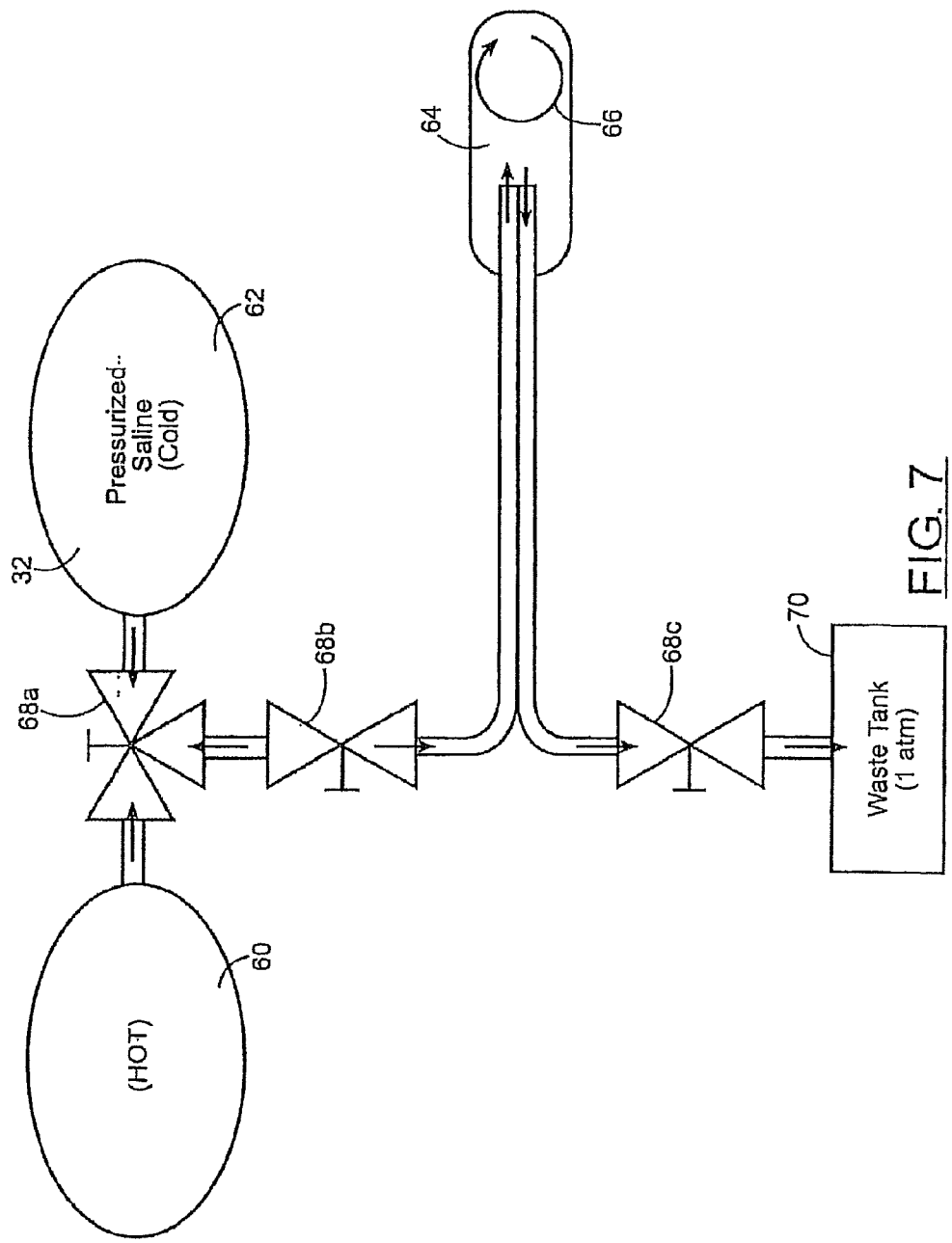
FIG. 7 is a schematic representation of a device for heating and expanding the retractor of the present invention.

A more complex temperature-controlled embodiment can also be utilized, as shown in FIG. 7. In one embodiment, a hot fluid 60 and a cold fluid 62 alternately are used to accelerate the solidification process and facilitate device removal. Such an embodiment can utilize a balloon 64 that is not only finable with pressurized fluid, for example a saline solution, but also circulates 66 the fluid through the balloon. Circulating the fluid continuously also is believed to confer additional advantages, because the body tissues around tube 10 tend to create a sizeable heat sink and the heat transfer to tube 10 from the fluid within the balloon may not be adequate to counter such a large heat sink unless the temperature of the fluid can be maintained. Such a device would have valve 68a with which to choose whether cold or hot fluid was being circulated within the balloon 64. The respective hot and cold fluid (60 and 62) can be adjusted to a desired temperature using heat exchangers (not shown), such as running the fluid lines through an ice bath and/or through an electric heater exchanger. Further a waste tank 70 would be provided so that fluid, previously circulated within balloon 64, could be removed therefrom, for example so as to deflate balloon 64 once retractor 10 is expanded to its desired size.

In the example of FIG. 7, the circulating hot or cold fluid passes to the balloon through inlet valve 68b and from the balloon through outlet valve 68c. One or both of these valves can have variable dimensions. With variable rates of inflow and/or outflow, three conditions are achieved: (1) with more flow through the inlet valve than the outlet valve, pressure in the balloon would be created causing the balloon to inflate, (2) with equal inlet and outlet valve flow rates, the balloon would maintain its volume but would have circulating fluid within, (3) with greater flow through the outlet valve 68c than the inlet valve 68b, the balloon 64 deflates. Valve 68a for the inlet fluid supply enables the user to select hot or ice-cold fluid, 60, 62 respectively. In some embodiments, the valves can be actuated by computerized control. In some embodiments, pressure can be controlled and desired inflow and outflow maintained using inflow and outflow circulating pumps (not shown). The circulating pumps can be powered by a separate pneumatic pump (not shown). In some embodiments, the fluid can be recirculated at least part of the time instead of removing it to waste tank 70. For inflating the balloon to its largest dimension, hot fluid circulates in the balloon. For accelerating the transition of the thermally responsive material of tube 10 to rigidity, it may be desirable to switch to cold fluid. For removing the retractor at the end of the procedure, hot fluid may again be used to re-inflate the balloon and soften the thermally responsive material.

Figure 13:
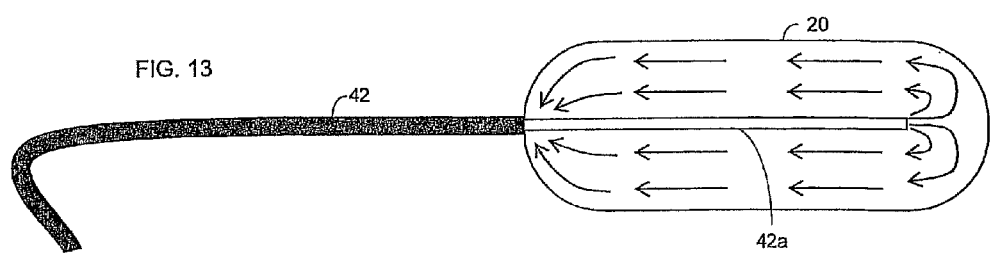
FIG. 13 is a schematic representation of one embodiment of a balloon connected to a fluid supply line.

FIG. 13 is a schematic representation illustrating one embodiment for configuring balloon 20 on the end of a fluid supply line 42. It is a coaxial design with the fluid such as saline entering the balloon 20 through a center tube 42a and exiting peripherally at the proximal end of the balloon 20, as illustrated in FIG. 13 with arrows showing the direction of fluid flow. As discussed above with respect to balloon 20, lubricating the fluid supply line 42 with a biocompatible material will make it easier to extract.

Figure 14A:
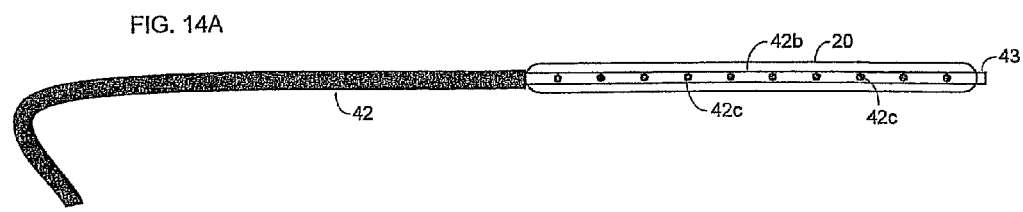
FIG. 14A is a schematic representation of another embodiment of a balloon connected to a fluid supply line.
Figure 14B:
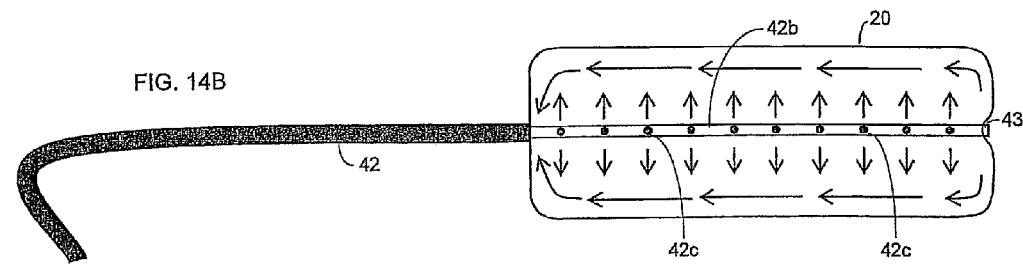
FIG. 14B is a schematic representation of the embodiment of FIG. 14A with the balloon inflated.

Another embodiment is illustrated in FIGS. 14A and 14B. It is also a coaxial design with the fluid entering the balloon 20 through an inner tube 42b. Inner tube 42b is capped at its distal end 43 but has one or more holes 42c for the fluid to exit in the region of inner tube 42b that is within the balloon 20. The inner tube 42b is connected to the balloon 20 near the distal end 43 to provide more rigidity for insertion against tissue. FIG. 14A illustrates this embodiment with the balloon 20 deflated. FIG. 14B illustrates this embodiment with the balloon 20 inflated, and with arrows showing the direction of fluid flow. As illustrated in FIG. 14B, the inflated balloon 20 can be shaped so as not to expand and pull away where the balloon 20 is connected to the inner tube 42b near the distal end 43, but to bulge distally to occupy space around that distal end 43. This feature may be important if a rigid inner tube 42b is desired, yet the surgeon wishes to retract tissue to the same depth that the inner tube 42b is inserted.

Figure 15A:
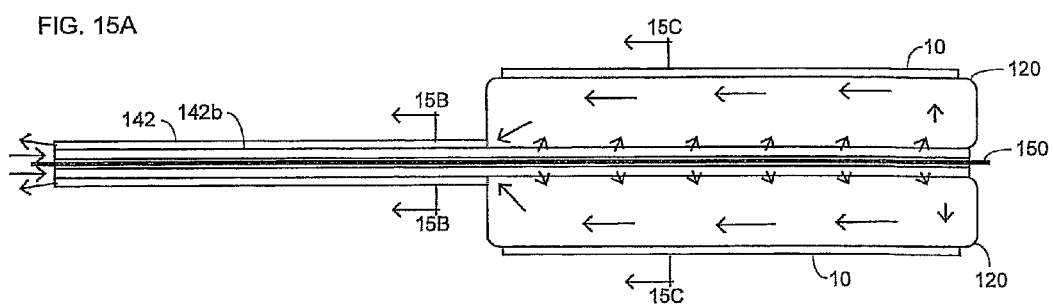
FIG. 15A is a schematic representation of a side cross-sectional view of a balloon connected to a fluid supply line inserted over a guide wire, with an inflated balloon surrounded by an expanded retractor tube.
Figure 15B:
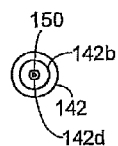
FIG. 15B is a cross-sectional view of the embodiment of FIG. 15A, taken along the line 15B-15B thereof.
Figure 15C:
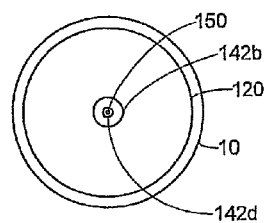
FIG. 15C is a cross-sectional view of the embodiment of FIG. 15A, taken along the line 15C-15C thereof.

Another embodiment is illustrated in FIGS. 15A-15C. FIG. 15A is a schematic representation of a side cross-sectional view with an inflated balloon 120 surrounded by an expanded retractor tube 10. A fluid supply line has an outer tube 142 surrounding a middle tube 142b that surrounds an inside tube 142d. The fluid supply line has a ring-shaped longitudinal cross-section, as represented in FIG. 15B. The passage between the middle tube 142b and the inside tube 142d is capped and sealingly connected to the balloon 120 near the distal end. The proximal end of the balloon 120 is sealingly connected to the end of the outer tube 142. FIG. 15C represents a longitudinal cross-sectional view of the inflated balloon 120. The arrows in FIG. 15A represent the direction of fluid flow. Fluid enters the balloon 120 through holes in the region of the middle tube 142b that is within the balloon 120, and exits at the proximal end of the balloon 120 through the passage between the outer tube 142 and the middle tube 142b. A guide wire 150 can be inserted to a point of surgical interest. After the guide wire 150 is properly positioned, the inside tube 142d (surrounded by the middle tube 142b and either by the outer tube 142 or by the deflated balloon 120 and the unexpanded tube 10) can be slid over the guide wire 150. The balloon 120 then can be inflated and the tube 10 expanded as shown in FIG. 15A. In some embodiments, there are radio-opaque marks on the guide wire 150, the middle tube 142b and/or on the inside tube 142d to show the depth of insertion relative to anatomical structures on a fluoroscopy image. Knowledge of the depth of insertion will help the surgeon to select the correct length for the retractor tube 10 and to size other components that are necessary for surgery (such as screws, implants, etc.).

Figure 16:
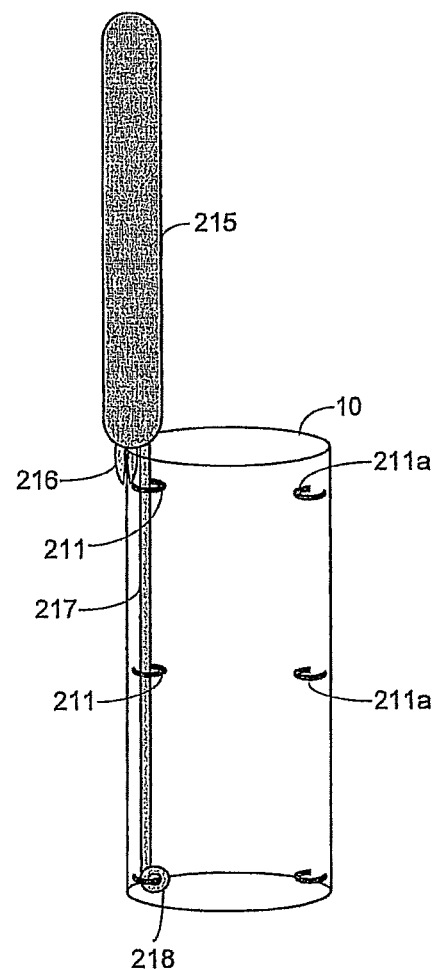
FIG. 16 is a schematic representation of a retractor tube with a handle for re-orienting the retractor.

In some embodiments, as represented in FIG. 16, a handle 215 can be attached to tube 10, that the surgeon can use to reposition tube 10 after it has been expanded. The handle 215 can be manipulated to re-orient the distal position of tube 10 to obtain a desired view of the surgical field without changing the proximal position of tube 10. In some embodiments, the handle 215 can be attached to a proximal end of tube 10 only with a clip 216. In other embodiments, a guiding mechanism is positioned longitudinally down an inner surface of tube 10, and moves radially outward as the tube 10 is expanded. The guiding mechanism can be a series of loops 211 as shown in FIG. 16. After the tube 10 is expanded, handle 215 can be attached and an extension rod 217 can extend from the handle 215 through the loops 211. The distal end of the rod 217 can comprise a hook or a latch 218 for securing the rod 217 to the bottom loop 211. Loops 211 can be made of cloth, wire, or other material, and can be rigid or flexible. As shown in FIG. 16, there can be a second series of loops 211*a* that are positioned longitudinally down the inner surface of tube 10 at different point on the inner circumference of tube 10 than the series of loops 211 are positioned. Another extension rod can extend through the loops 211*a*, and can be connected to the same handle 215 or to a second handle. In other embodiments (not shown), the guiding mechanism can be one or more continuous channels along an inner surface of tube 10, and rod 17 can extend through the channels instead of through loops 211. In some embodiments, one or more rods 217 can be inserted through the guiding mechanism before tube 10 is expanded, but that increases the diameter of the unexpanded tube 10.

Following surgery, tube 10 can be removed in a variety of ways. In some applications, tube 10 can be removed by simply pulling tube 10 out of the surgical corridor 18. In other applications, pulling tube 10 out will cause undesirable tissue damage at the surgical site. To avoid tissue damage, in one embodiment, tube 10 can be made of a material having a transition temperature low enough to be tolerated by the tissues. In these applications, the surgical corridor may be filled with heated saline to cause softening of the malleable retractor walls and allow easy removal. In embodiments using retractors with a small diameter in the unexpanded state, the thermally responsive material returning to its original shape upon re-heating will aid removal. Upon introduction of heated saline, tube 10 would return to a small diameter for easy removal. In other embodiments, a heating wire or a tool with a heated tip may be used to create seams in tube 10 from the inside. Following creation of seams, tube 10 may be broken out of the surgical corridor in pieces. Tube 10 can carry additional perforations laterally 10*p* to facilitate this "unzipping" maneuver. Such an application would be particularly useful, for example, where the transition temperature of tube 10 material is so high that introduction of heated saline solution into the corridor would cause undesired tissue damage.

In some applications, bleeding may occur upon removal of tube 10. In one embodiment, shown in FIG. 5, bleeding is mitigated by coating the tube 10 and/or balloon 20 (or other insufflating means) with a hemostatic agent 52 such as, for example, gel foam prior to insertion. For example, the tube 10 and balloon 20 could be coated by rolling them in a tray of the hemostatic agent. In some applications, it may also be necessary to utilize lubricants, sheaths, or other coatings to prevent adhesion of the tube and insufflator to surrounding tissues. Such adhesion may occur when using a hemostatic agent in some applications.

Figure 10A:
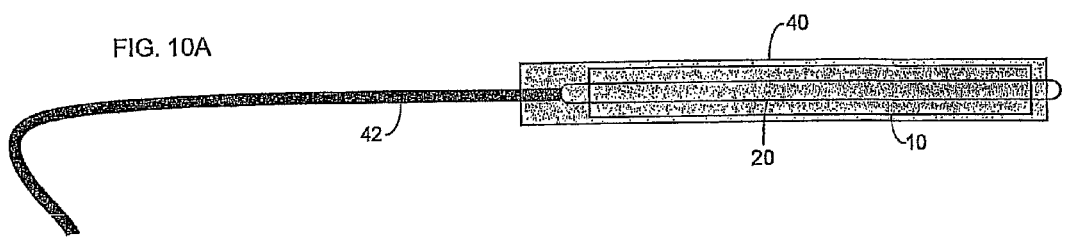
FIG. 10A is a schematic representation of a balloon retractor device including a sheath and with the balloon deflated.
Figure 10B:
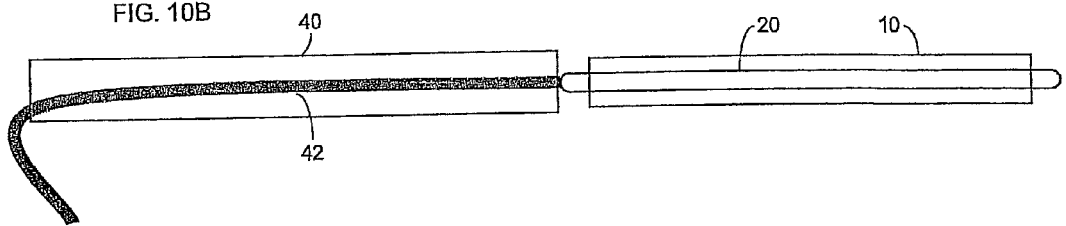
FIG. 10B is a schematic representation of the balloon retractor device of FIG. 10A with the sheath retracted.
Figure 10C:
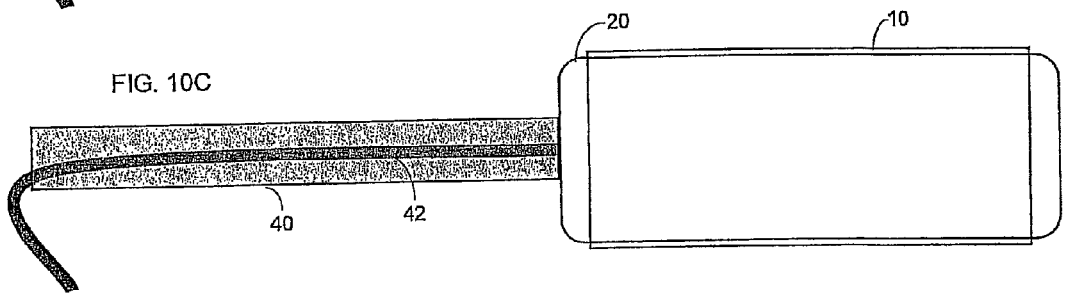
FIG. 10C is a schematic representation of the balloon retractor device of FIG. 10B with the balloon inflated.

Balloon 20 is deflated and tube 10 is softened at the time of insertion, and tube 10 may not be sufficiently rigid. In some embodiments, the tube 10 can be enclosed in a cylindrical sheath 40, as illustrated in FIG. 10A. Sheath 40 may have a tapered leading edge. Sheath 40 may be comprised of metal, plastic, or other material of adequate rigidity. Sheath 40 enables easier insertion into the surgical site. In some embodiments, there are radio-opaque marks on the sheath 40 to show the depth of insertion relative to anatomical structures on a fluoroscopy image. Sheath 40 can be retracted back over a fluid supply line 42 (as illustrated in FIG. 10B), allowing the balloon 20 then to be expanded as described previously (as illustrated in FIG. 10C). An interior surface of sheath 40 can be lubricated so that it retracts smoothly over tube 10.

When inserting a tube 10 into a surgical site, the surgeon would rely on fluoroscopy and direct visualization of the surgical area, but little would be known about the local environment around a tip of the tube 10. In some embodiments, a small sensor 46 (such as a fiber optic sensor or a camera) is mounted at the tip of the tube 10, as illustrated in FIG. 12, to make it easier for the surgeon to know whether critical internal structures are being approached. A transmission line 48 (such as an optical fiber) for transmitting signals from the sensor 46 is routed adjacent the deflated balloon 20 inside of the tube 10, and then along a fluid supply line 42 to necessary support equipment. The surgeon can watch a monitor while inserting the tube 10. After the tube 10 is positioned where desired, the surgeon can remove the line 48 and sensor 46 before inflating the balloon 20, if it is undesirable for the line 48 or the sensor 46 to be compressed by the balloon 20.

If a tube 10 is made of a thermoplastic material or an SMA that requires heating to a potentially dangerous temperature, tube 10 can be insulated from the surrounding tissue. In some embodiments, a thin elastic thermal barrier 44 surrounds the tube 10, as illustrated in FIGS. 11A and 11B. Barrier 44 remains positioned between the tube 10 and the tissue at all times. Being elastic, barrier 44 stretches as the tube 10 is expanded, as illustrated in FIGS. 11A and 11B. Barrier 44 serves as a thermal barrier to prevent the heated tube 10 from damaging the tissue with which it otherwise would be in contact.

Figure 19:
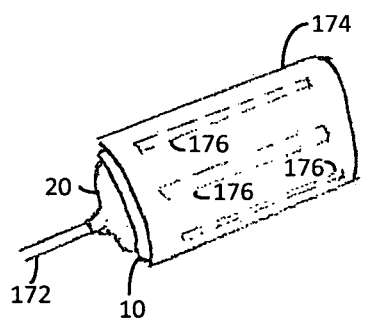
FIG. 19 is a perspective view of a balloon retractor device with the tube surrounded by a thermal barrier reinforced with embedded ribs.

In an embodiment shown in an expanded state in FIG. 19, elastic thermal barrier 174 surrounds tube 10, which surrounds balloon 20 which is attached to fluid supply line 172. Thermal barrier 174 is reinforced with embedded metal ribs 176 (shown in phantom) which help to make the deflated balloon stiffer and, consequently, enable easier manual insertion in an area of desired retraction. The ribs 176 are axial so as not to interfere with radial expansion of the balloon 20. The ribs 176 also are radio-opaque, allowing the surgeon to monitor the progress of the insertion with fluoroscopy.

FIGS. 20A-22C illustrate use of a thermal barrier loader 180 to facilitate insertion of a balloon 20 and tube 10 into a thermal barrier 184, prior to introduction into the surgical incision. A thermoplastic tube can be heated to render it pliable by soaking it in a sterile hot water bath. It may not be necessary to use a thermal barrier loader if, for example, a tube and balloon come pre-loaded with a thermal barrier. However, that pre-loading inhibits heating of the tube without also elevating the temperature of the thermal barrier.

Figure 20A:
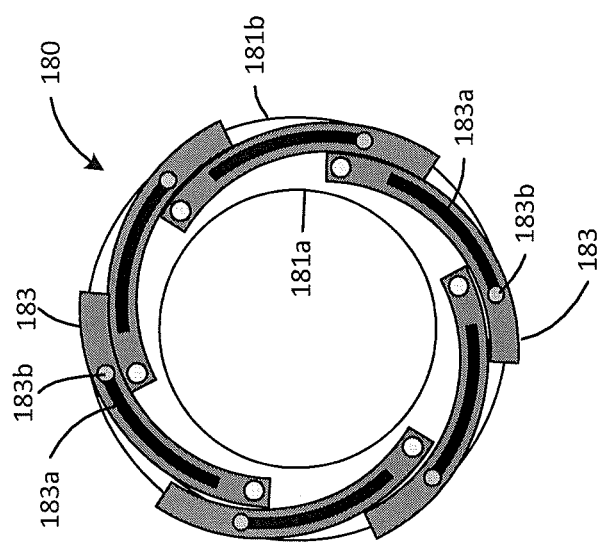
FIG. 20A is an end view of a thermal barrier loader in a radially contracted state.
Figure 20B:
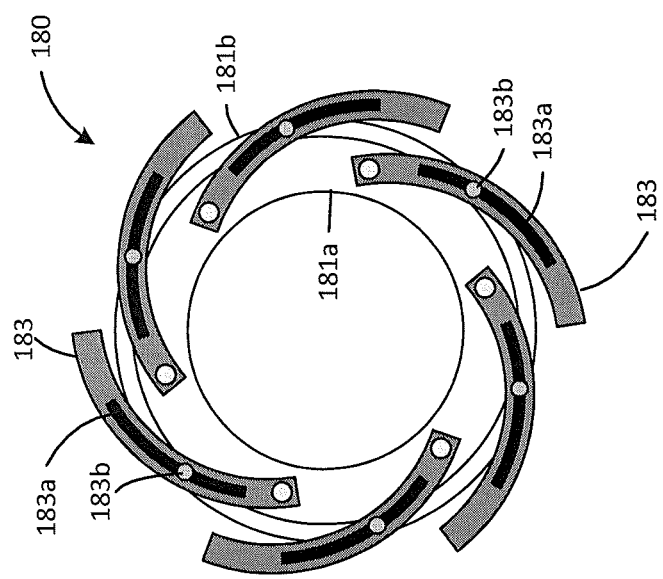
FIG. 20B is an end view of the thermal barrier loader of FIG. 20A in a radially intermediate state.
Figure 20C:
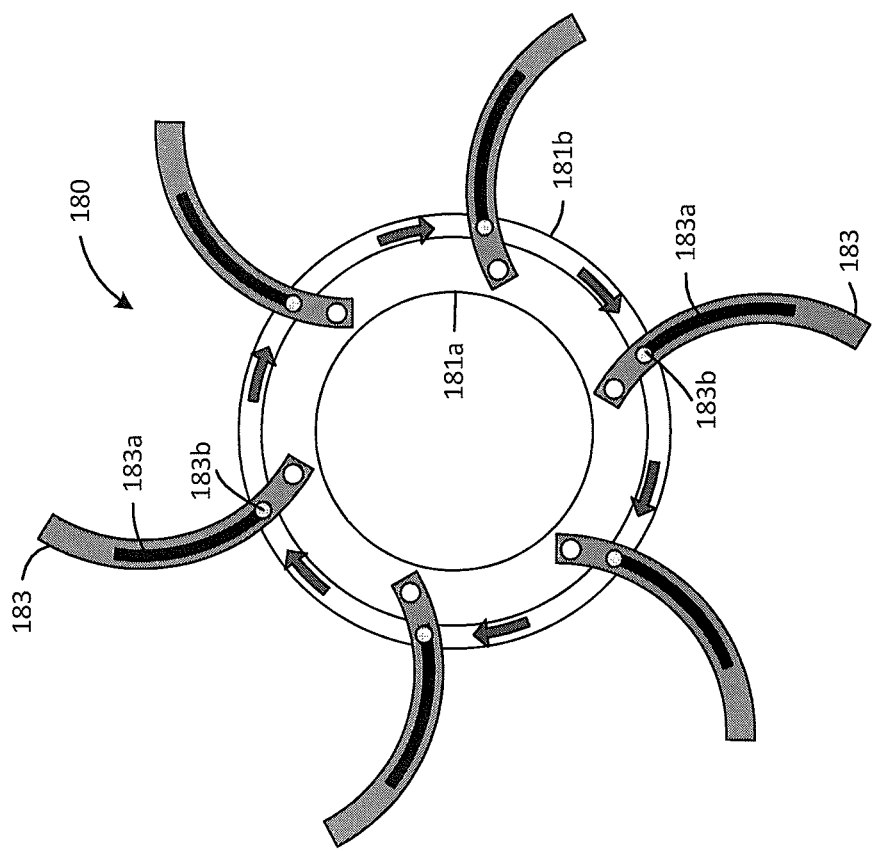
FIG. 20C is an end view of the thermal barrier loader of FIG. 20A in a radially expanded state.
Figure 21:
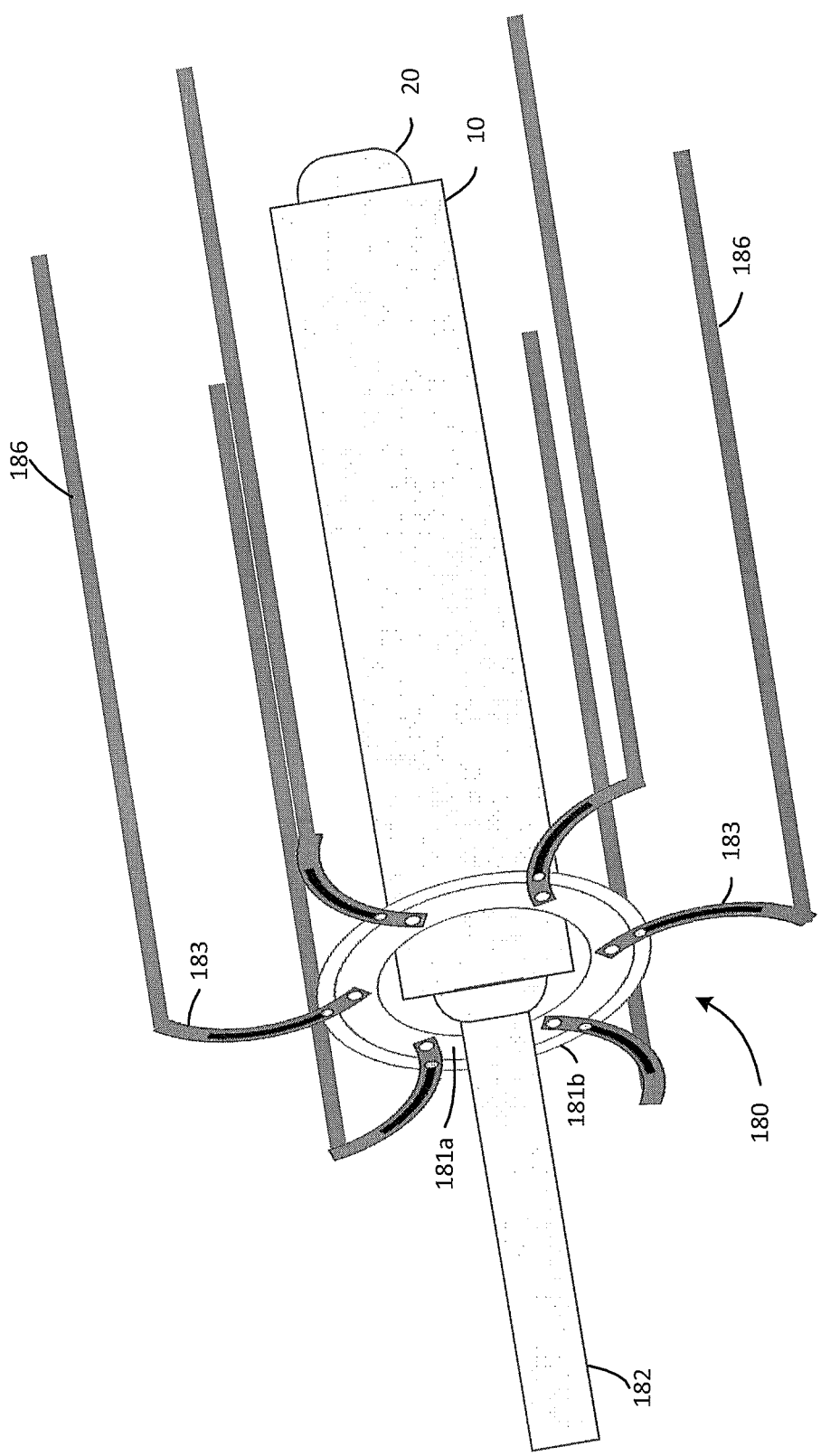
FIG. 21 is a schematic representation of the thermal barrier loader of FIG. 20A in relation to a balloon retractor device.

FIGS. 20A-20C show an end view of thermal barrier loader 180. There are concentric inner and outer rings 181*a* and 181*b*, with prongs 183 pivotally attached to inner ring 181*a*. Each prong 183 includes a slot 183*a*. A pin 183*b* slides in a respective slot 183*a*, and is attached to outer ring 181*b*. As shown in FIGS. 20A, 20B and 20C, as outer ring 181*b* is rotated relative to inner ring 181*a*, each pin 183*b* slides within its respective slot 183*a* and the prongs 183 pivot out or in radially. As shown in FIG. 21, an axial stiffener 186 is attached to the end of each prong 183, and extends perpendicular to a plane generally defined by prongs 183 and by rings 181a and 181b. FIG. 21 also shows that tube 10, which surrounds balloon 20 that is attached to fluid supply line 182, can fit through inner ring 181a.

Figure 22A:
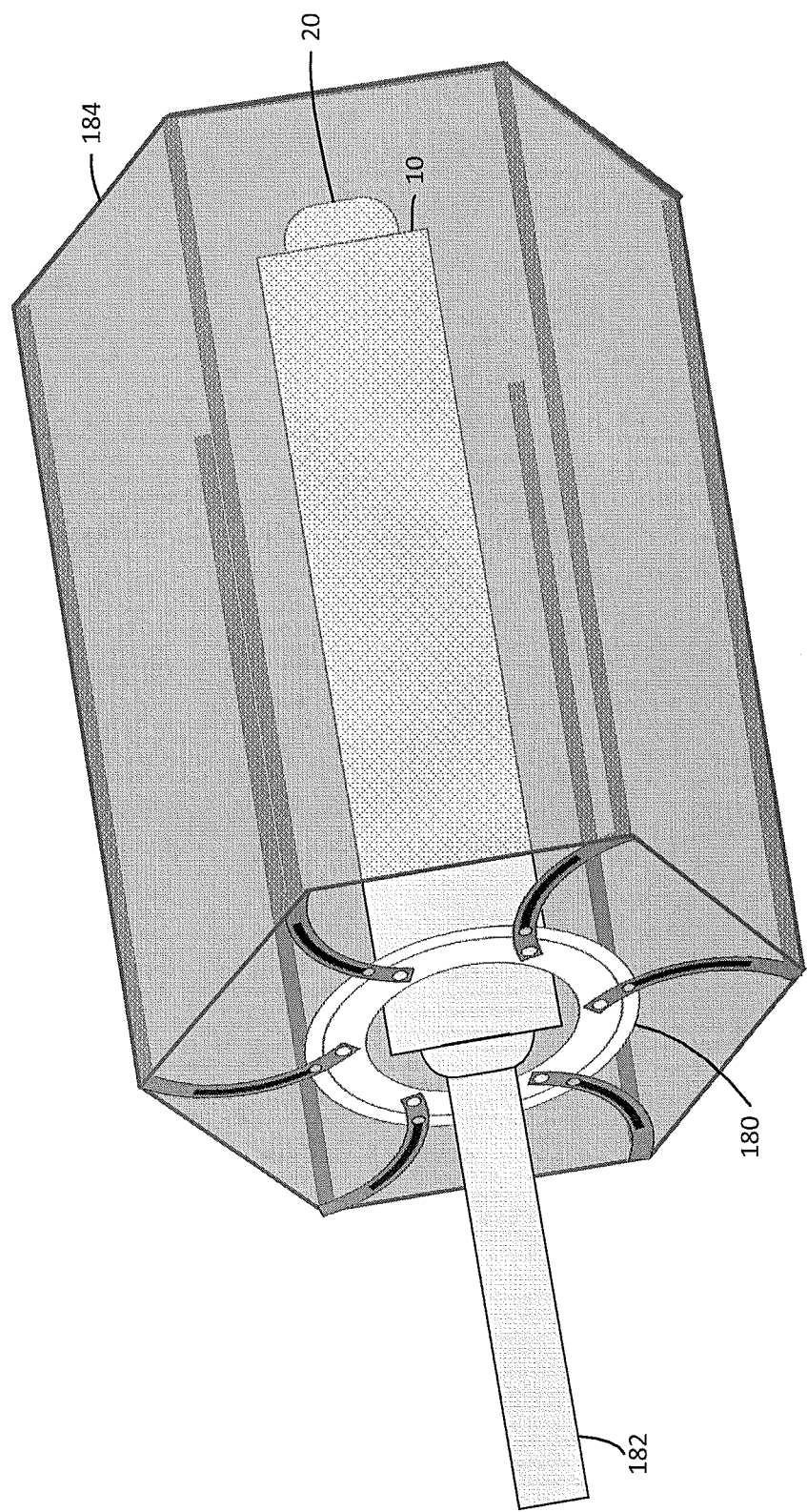
FIG. 22A is a schematic representation of the thermal barrier loader of FIG. 20A in a radially expanded state, with a thermal barrier fitted over a balloon retractor device.
Figure 22B:
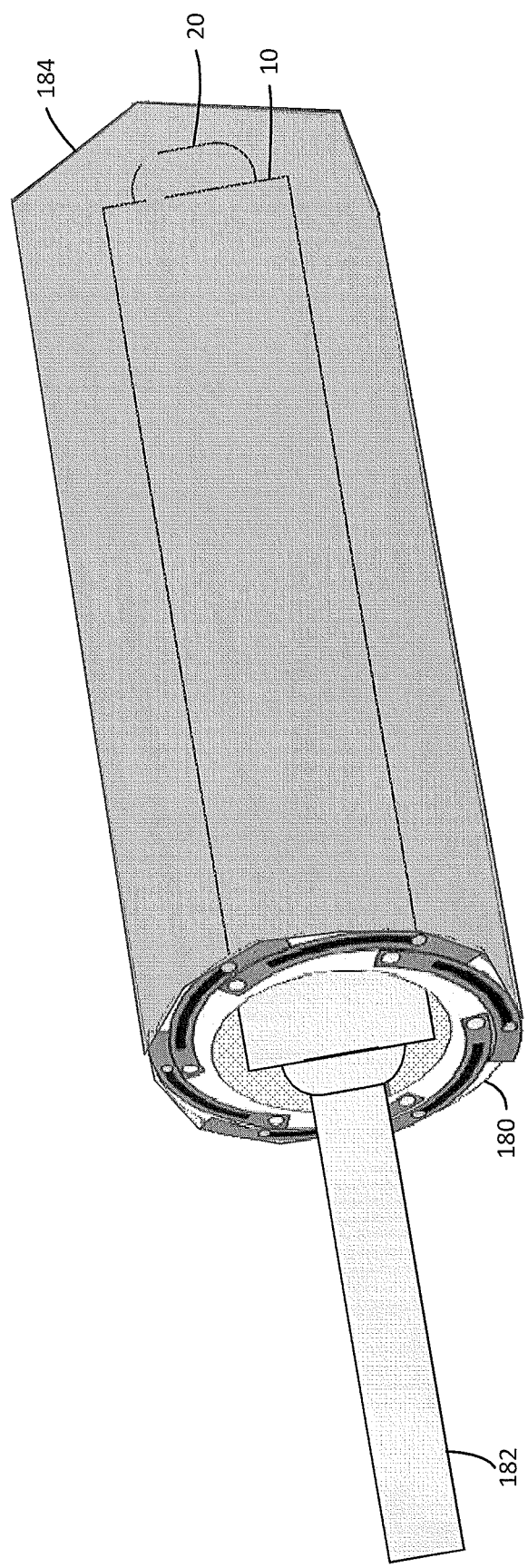
FIG. 22B is a schematic representation of the thermal barrier loader of FIG. 20A in a radially contracted state, with a thermal barrier fitted over a balloon retractor device.
Figure 22C:
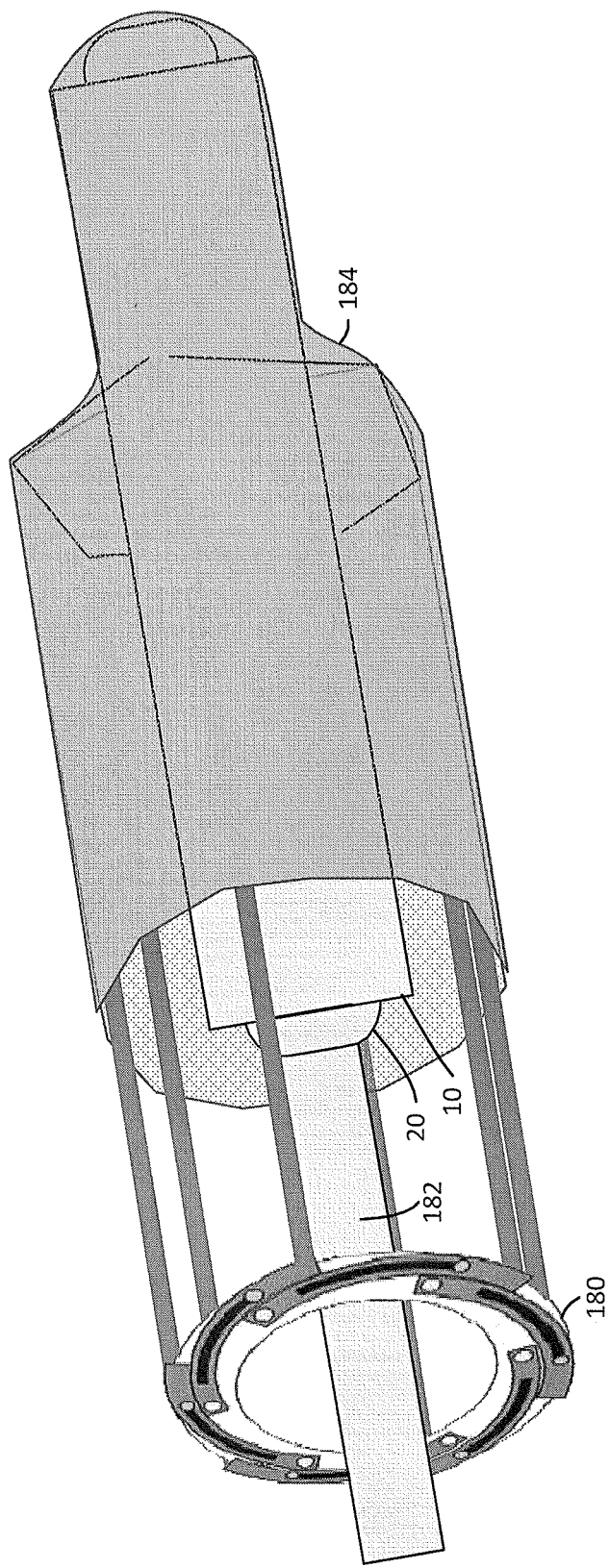
FIG. 22C is a schematic representation of the thermal barrier loader of FIG. 20A, showing it being removed and leaving the thermal barrier fitted over a balloon retractor device.

FIG. 22A shows thermal barrier loader 180 in a radially expanded state, with elastic thermal barrier 184 fitted over axial stiffeners 186. Thermal barrier 184 may be fitted over axial stiffeners 186 before rings 181a and 181b are rotated to radially expand thermal barrier 184. Thermal barrier 184 is radially expanded to facilitate insertion of tube 10 into thermal barrier 184, by passing tube 10 through inner ring 181a. Tube 10 surrounds balloon 20 which is attached to fluid supply line 182. FIG. 22B shows thermal barrier loader 180 in a radially contracted state after insertion of tube 10 into thermal barrier 184. FIG. 22C shows thermal barrier loader 180 being slid back over fluid supply line 182, leaving elastic thermal barrier 184 fitted over tube 10.

In another embodiment, axial ribs embedded in a thermal barrier may comprise the axial stiffeners used with a thermal barrier loader, with an end of each axial rib being removably attachable to an end of a prong of the thermal barrier loader. In that case, the ends of the axial ribs are attached to the ends of the prongs, respectively, before radial expansion of the thermal barrier and insertion of the tube. After insertion of the tube, the ends of the axial ribs can be detached from the prongs and the thermal barrier loader can be slid back over the fluid supply line, leaving the elastic thermal barrier and its embedded axial ribs fitted over the tube.

An example of using thermal barrier loader 180 in conjunction with balloon inflation/deflation mechanism 161 follows: A thermoplastic tube 10 surrounding a balloon 20 is soaked in a sterile hot water bath to render the tube pliable and ready for expansion. An elastic thermal barrier is fitted over the thermal barrier loader 180, and the balloon is attached to the inflation/deflation mechanism 161. At an appropriate time for introduction into the surgical incision, tube 10 is passed through inner ring 181a and thermal barrier loader 180 is slid back, leaving the thermal barrier fitted over tube 10 which is introduced into the surgical incision. When the surgeon determines that tube 10 has been placed at the desired position, trigger 162 is used to cause the cold gas to inflate balloon 20 and expand tube 10. When the tube is cooled and hardened, valve 163 is switched to deflation mode and trigger 162 is used to vacuum gas out of balloon 20 and into waste depository 167, pulling the skin of balloon 20 away from the hardened tube 10. Balloon 20 is withdrawn from the surgical field, leaving the hardened and expanded tube 10 surrounded by the elastic thermal barrier. The surgeon can cut through the thermal barrier if it has a closed end, and tube 10 provides a surgical corridor. After surgery, tube 10 can be pulled out of the surgical incision. Alternatively, a heated balloon 20 can inserted into tube 10 to render it pliable, or tube 10 may be removed in pieces using a cutting tool or using a heating wire or a tool with a heated tip to create seems in tube 10. Another alternative is that one or more wires embedded in the inside surface of the thermal barrier or in tube 10 can be heated electrically.

It will be readily recognized by one skilled in the art that the invention may be optimized and is well suited for usage with a surgical robot. A surgical robot can be utilized to hold and position a rigid straight or curved extension with the balloon and retractor on its tip, then move the balloon into exact position based on medical images. It can also be used, for example, to precisely adjust the rotational position of the retractor tube if an asymmetrical shape (for example, half-cylinder shape) is needed for a particular retraction. Both position and orientation may be more accurately controlled by a surgical robot than manually in certain applications.

Although illustrative embodiments of the invention have been shown and described, it is to be understood that various modifications and substitutions may be made by those skilled in the art without departing from the novel spirit and scope of the invention, and that particular features discussed in connection one embodiment will also be recognized as suitable in connection with a different embodiment.

What is claimed is:

1. A surgical retractor system for maintaining a surgical corridor, the system comprising a surgical retractor device for insertion through a skin surface to a point of surgical interest, the surgical retractor device comprising:
   a tube of thermally responsive material that is pliable and expansive when heated to a transition temperature that is above body temperature, and that is rigid when cooled below the transition temperature;
   a balloon that is removably fitted in the tube; and
   an elastic thermal barrier that is fitted around the tube to thermally insulate the tube from surrounding tissue;
   wherein the surgical retractor device can be inserted through the skin surface to the point of surgical interest while the tube has a relatively narrow diameter compared to its diameter in an expanded state; and
   wherein, while the surgical retractor device is inserted to the point of surgical interest, the balloon and the tube can be expanded while the tube remains pliable, and the expanded tube can be cooled so as to render the tube rigid.

2. The surgical retractor system of claim 1, further comprising:
   a thermal barrier loader for facilitating insertion of the tube into the elastic thermal barrier;
   wherein the thermal barrier loader can stretch the elastic thermal barrier wide enough to permit easy fitting of the thermal barrier around the tube; and
   wherein the thermal barrier loader can be detached from the thermal barrier before insertion of the surgical retractor device to the point of surgical interest.

3. The surgical retractor system of claim 2, wherein the thermal barrier loader comprises:
   at least one ring through which the tube can be inserted into the elastic thermal barrier;
   a plurality of moveable prongs that can extend radially outward from the at least one ring; and
   a plurality of axial stiffeners attached, respectively, to ends of the prongs, the axial stiffeners being aligned perpendicular to a plane generally defined by the prongs;
   wherein distances between the axial stiffeners determine a width that the elastic thermal barrier is stretched by the thermal barrier loader, to permit fitting of the thermal barrier around the tube.

4. The surgical retractor system of claim 1, further comprising:
   a balloon inflation/deflation mechanism;
   wherein the balloon inflation/deflation mechanism inflates the balloon by releasing refrigerant into the balloon, where the refrigerant is in a pressurized liquid state before release and vaporizes into a cold gas when released.

5. The surgical retractor system of claim 4, wherein the balloon inflation/deflation mechanism deflates the balloon by releasing and vaporizing the refrigerant through a corridor that is configured such that gas movement pulls a vacuum on the balloon.

6. The surgical retractor system of claim 1, wherein the thermally responsive material is a thermoplastic material with a transition temperature of about 50° C.

7. The surgical retractor system of claim 1, wherein the thermally responsive material is polycaprolactone.

8. The surgical retractor system of claim 1, wherein electric wires are embedded in the tube for electric heating of the tube.

9. The surgical retractor system of claim 1, wherein the thermal barrier comprises axial reinforcing ribs.

10. The surgical retractor system of claim 9, wherein the axial ribs are radio-opaque.

11. The surgical retractor system of claim 1, wherein a shape of the expanded tube is dictated in part by a shape of the balloon.

12. The surgical retractor system of claim 1, wherein a shape of the expanded tube is dictated in part by varying wall thickness or composition of the material in a portion of a wall in a specified region of the tube.

13. The surgical retractor system of claim 1, wherein a distal tip of the tube is radio-opaque to allow fluoroscopic verification of its placement in situ.

14. The surgical retractor system of claim 1, wherein the surgical retractor device further comprises an illuminator and a light sensor to provide an indication of placement in situ.

15. The surgical retractor system of claim 1, further comprising at least one handle that is structured and dimensioned for attachment to the surgical retractor device for use in repositioning the tube after it has been expanded.

16. A method of maintaining a surgical corridor through a skin surface to a point of surgical interest, the method comprising:
   providing a tube of thermally responsive material that is pliable and expandable when heated to a transition temperature that is above body temperature, and that is rigid when cooled below the transition temperature;
   removably fitting a balloon in the tube;
   warming the tube to at least the transition temperature;
   fitting an elastic thermal barrier around the tube to thermally insulate the tube from surrounding tissue;
   after the tube is surrounded by the thermal barrier, inserting the tube through the skin surface to the point of surgical interest while the tube has a relatively narrow diameter compared to its diameter in an expanded state;
   while the tube is inserted to the point of surgical interest, expanding the balloon and the tube while the tube remains pliable; and
   cooling the expanded tube to render it rigid.

17. The method of claim 16, wherein the step of fitting the thermal barrier around the tube comprises:
   using a thermal barrier loader to stretch the elastic thermal barrier wide enough to permit easy fitting of the thermal barrier around the tube;
   inserting the tube through the thermal barrier loader and into the thermal barrier; and
   detaching the thermal barrier loader, leaving the thermal barrier surrounding the tube.

18. The method of claim 16, wherein in the warming step comprises soaking the tube in a sterile hot water bath.

19. The method of claim 16, wherein the expanding and cooling steps comprise inflating the balloon by releasing refrigerant into the balloon, where the refrigerant is in a pressurized liquid state before release and vaporizes into a cold gas when released.

20. The method of claim 16, further comprising extracting the balloon from inside of the tube after the expanded tube is cooled and rendered rigid.

21. The method of claim 16, further comprising deflating the balloon, after the expanded tube is cooled and rendered rigid, by releasing and vaporizing a refrigerant through a corridor that is configured such that gas movement pulls a vacuum on the balloon, where the refrigerant is in a pressurized liquid state before release and vaporizes into a cold gas when released.

22. The method of claim 16, further comprising re-heating the tube to the transition temperature, to render the tube pliable and to facilitate removal of the tube from the point of surgical interest.

23. The method of claim 22, wherein the re-heating comprises applying an electrical potential to electric wires embedded in the tube.

24. The method of claim 16, further comprising creating seams in the tube using a tool with a heated tip to facilitate removal of the tube from the point of surgical interest.

25. The method of claim 16, wherein the inserting step further comprises using a surgical robot to move the tube into a desired position and orientation at the point of surgical interest.

* * * * *